US012748117B2

(12) United States Patent
Cerón Madrigal et al.

(10) Patent No.: US 12,748,117 B2

(45) Date of Patent: Sep. 29, 2026

(54) MONOCLONAL ANTIBODY AND POLYCLONAL ANTIBODY AND OXYTOCIN QUANTIFICATION METHOD BASED ON SAME

(71) Applicant: UNIVERSIDAD DE MURCIA, Murcia (ES)

(72) Inventors: José Joaquín Cerón Madrigal, Murcia (ES); Silvia Martínez Subiela, Murcia (ES); Marina López Arjona, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 951 days.

(21) Appl. No.: 17/995,125

(22) PCT Filed: Mar. 30, 2021

(86) PCT No.: PCT/ES2021/070221

§ 371 (c)(1),
(2) Date: Sep. 30, 2022

(87) PCT Pub. No.: WO2021/198548

PCT Pub. Date: Oct. 7, 2021

(65) Prior Publication Data

US 2023/0168258 A1 Jun. 1, 2023

(30) Foreign Application Priority Data

Apr. 1, 2020 (ES) .................................. 202030265

(51) Int. Cl.
*G01N 33/74* (2006.01)
*C07K 16/26* (2006.01)

(52) U.S. Cl.
CPC ............ *G01N 33/74* (2013.01); *C07K 16/26* (2013.01); *C07K 2317/565* (2013.01)

(58) Field of Classification Search
None
See application file for complete search history.

(56) References Cited

PUBLICATIONS

Lopéz-Arjona et al. (2024, PLoS ONE 19(4):e0297539; pp. 1-16).*
Jagla et al. (2000, FASEB J 14:1126-1131).*
Leng et al. (2016, J Neuroendocrinol 28(10):10.1111/jne.12413; pp. 1-13).*
Brandtzaeg et al., Proteomics tools reveal startlingly high amounts of oxytocin in plasma and serum. Scientific Reports. 2016, vol. 6, Article No. 31693. 1-7.
Burgeon et al., Monoclonal antibodies to oxytocin: production and characterization. Journal of Neuroimmunology. 1991, vol. 31, No. 3, pp. 235-244.
Gruson. Oxytocin testing and reproductive health: Status and clinical applications. Clin Biochem. 2018;62:55-61.
Haraya et al., Development of a highly specific enzyme immunoassay for oxytocin and its use in plasma samples. Annals of Clinical Biochemistry. 2017, vol. 54, No. 1, pp. 101-106.
International Preliminary Report on Patentability for PCT/ES2021/070221. Mailed Aug. 17, 2022. 13 pages.
International Search Report and Written opinion for PCT/ES2021/070221. Mailed Jul. 14, 2021. 22 pages.
Leng et al., Measuring oxytocin and vasopressin: bioassays, immunoassays and random numbers. Journal of Neuroendocrinology. 2016, vol. 28, No. 10, Article No. 10.1111/jne.12413. 1-13.
Lopez-Ajona et al., Ejaculate collection influences the salivary oxytocin concentrations in breeding male pigs. Animals. 2020, vol. 10, No. 8, Article No. 1268. 1-12.
Lopez-Arjona et al., Changes in oxytocin concentrations in saliva of pigs after a transport and during lairage at slaughterhouse. Research in Veterinary Science. 2020, vol. 133, pp. 26-30.
Lopez-Arjona et al., Effect of reduction and alkylation treatment in three different assays used for the measurement of oxytocin in saliva of pigs. Domestic Animal Endocrinology. 2021, vol. 74, Article No. 106498. 8 pages.
Lopez-Arjona et al., Oxytocin in saliva of pigs: an assay for its measurement and changes after farrowing. Domestic Animal Endocrinology. 2020, 70, Article No. 106384. 1-4.
Lurzel et al., Salivary oxytocin in pigs, cattle, and goats during positive human-animal interactions. Psychoneuroendocrinology. 2020, vol. 115, Article No. 104636. 1-7.
Maclean et al., Challenges for measuring oxytocin: The blind men and the elephant? Psychoneuroendocrinology. 2019, vol. 107, pp. 225-231.
Maclean et al., Validation of salivary oxytocin and vasopressin as biomarkers in domestic dogs. J Neurosci Methods. 2018, 293, 67-76.
Salzet et al., Epitope mapping with ELISA of an antibody against oxytocin used for the characterization of an oxytocin-like epitope in the sex segmental ganglia of the leech Erpobdella octoculata. Comp Biochem Physiol Comp Physiol. 1993;104(1):75-81.
Szeto et al., Evaluation of enzyme immunoassay and radioimmunoassay methods for the measurement of plasma oxytocin. Psychosomatic Medicine. 2011, vol. 73, No. 5, pp. 393-400.

* cited by examiner

*Primary Examiner* — Thomas J. Visone
(74) *Attorney, Agent, or Firm* — Casimir Jones, S.C.; Tristan A. Fuierer

(57) ABSTRACT

The present invention relates to an in vitro method for the quantification of free oxytocin, protein-bound oxytocin that can be released in a reduction/alkylation treatment, and protein-bound oxytocin, in a sample, without performing a reduction/alkylation treatment, wherein said method comprising carrying out a first assay using a monoclonal antibody that binds specifically to free oxytocin and to protein-bound oxytocin that can be released in a reduction/alkylation treatment, and carrying out a second assay using a polyclonal antibody that binds specifically to protein-bound oxytocin. The invention also relates to the monoclonal antibody and polyclonal antibody, and to a composition and kit comprising same.

17 Claims, 2 Drawing Sheets

Specification includes a Sequence Listing.

SEQUENCE LISTING

<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Cys Tyr Ile Gln Asn Cys Pro Leu Gly
1 5

<210> SEQ ID NO 2
<211> LENGTH: 136
<212> TYPE: PRT
<213> ORGANISM: Artificial Sequence
<220> FEATURE:
<223> OTHER INFORMATION: Synthetic Construct

<400> SEQUENCE: 2

Met Asp Trp Leu Trp Asn Leu Leu Phe Leu Met Ala Ala Ala Gln Ser
1 5 10 15

Ile Gln Ala Gln Ile Gln Leu Val Gln Ser Gly Pro Glu Leu Lys Lys
20 25 30

Pro Gly Glu Thr Val Lys Ile Ser Cys Lys Ala Ser Gly Tyr Ile Phe
35 40 45

Thr Asn Tyr Gly Met Asn Trp Val Lys Gln Ala Pro Gly Lys Asn Leu
50 55 60

Lys Trp Met Gly Trp Ile Asn Thr Asn Thr Gly Glu Pro Thr Tyr Ala
65 70 75 80

Glu Glu Phe Lys Gly Arg Phe Ala Phe Ser Leu Glu Thr Ser Ala Ser
85 90 95

Ile Ala Tyr Leu Lys Ile Asn Asn Leu Lys Asn Glu Asp Thr Ala Thr
100 105 110

Tyr Phe Cys Ser Arg Gly Gly Leu Leu Pro Leu Ser Tyr Trp Gly Gln
115 120 125

Gly Thr Leu Val Thr Val Ser Ala
130 135

<210> SEQ ID NO 3
<211> LENGTH: 117
<212> TYPE: PRT
<213> ORGANISM: Artificial Sequence
<220> FEATURE:
<223> OTHER INFORMATION: Synthetic Construct

<400> SEQUENCE: 3

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Ile Phe Thr Asn Tyr
20 25 30

Gly Met Asn Trp Val Lys Gln Ala Pro Gly Lys Asn Leu Lys Trp Met
35 40 45

Gly Trp Ile Asn Thr Asn Thr Gly Glu Pro Thr Tyr Ala Glu Glu Phe
50 55 60

Lys Gly Arg Phe Ala Phe Ser Leu Glu Thr Ser Ala Ser Ile Ala Tyr
65 70 75 80

Leu Lys Ile Asn Asn Leu Lys Asn Glu Asp Thr Ala Thr Tyr Phe Cys
85 90 95

```
Ser Arg Gly Gly Leu Leu Pro Leu Ser Tyr Trp Gly Gln Gly Thr Leu
            100                 105                 110

Val Thr Val Ser Ala
        115


<210> SEQ ID NO 4
<211> LENGTH: 19
<212> TYPE: PRT
<213> ORGANISM: Artificial Sequence
<220> FEATURE:
<223> OTHER INFORMATION: Synthetic Construction

<400> SEQUENCE: 4

Met Asp Trp Leu Trp Asn Leu Leu Phe Leu Met Ala Ala Ala Gln Ser
1               5                   10                  15

Ile Gln Ala


<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr
            20                  25                  30


<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asn Tyr Gly Met Asn
1               5


<210> SEQ ID NO 7
<211> LENGTH: 14
<212> TYPE: PRT
<213> ORGANISM: Artificial Sequence
<220> FEATURE:
<223> OTHER INFORMATION: Synthetic Construct

<400> SEQUENCE: 7

Trp Val Lys Gln Ala Pro Gly Lys Asn Leu Lys Trp Met Gly
1               5                   10


<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Trp Ile Asn Thr Asn Thr Gly Glu Pro Thr Tyr Ala Glu Glu Phe Lys
1               5                   10                  15

Gly
```

```
<210> SEQ ID NO 9
<211> LENGTH: 32
<212> TYPE: PRT
<213> ORGANISM: Artificial Sequence
<220> FEATURE:
<223> OTHER INFORMATION: Synthetic Construct

<400> SEQUENCE: 9

Arg Phe Ala Phe Ser Leu Glu Thr Ser Ala Ser Ile Ala Tyr Leu Lys
1               5                   10                  15

Ile Asn Asn Leu Lys Asn Glu Asp Thr Ala Thr Tyr Phe Cys Ser Arg
            20                  25                  30


<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Gly Gly Leu Leu Pro Leu Ser Tyr
1               5


<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Trp Gly Gln Gly Thr Leu Val Thr Val Ser Ala
1               5                   10


<210> SEQ ID NO 12
<211> LENGTH: 131
<212> TYPE: PRT
<213> ORGANISM: Artificial Sequence
<220> FEATURE:
<223> OTHER INFORMATION: Synthetic Construct

<400> SEQUENCE: 12

Met Lys Leu Pro Val Arg Leu Leu Val Leu Met Phe Trp Ile Pro Ala
1               5                   10                  15

Ser Thr Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Phe Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Phe Pro Trp Thr Phe Gly Gly Gly Thr Lys Leu
        115                 120                 125

Glu Ile Lys
    130
```

<210> SEQ ID NO 13
<211> LENGTH: 112
<212> TYPE: PRT
<213> ORGANISM: Artificial Sequence
<220> FEATURE:
<223> OTHER INFORMATION: Synthetic Construct

<400> SEQUENCE: 13

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Phe Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Phe Pro Trp Thr Phe Gly Gly Gly Thr Lys Leu Glu Ile Lys
100 105 110

<210> SEQ ID NO 14
<211> LENGTH: 19
<212> TYPE: PRT
<213> ORGANISM: Artificial Sequence
<220> FEATURE:
<223> OTHER INFORMATION: Synthetic Construct

<400> SEQUENCE: 14

Met Lys Leu Pro Val Arg Leu Leu Val Leu Met Phe Trp Ile Pro Ala
1 5 10 15

Ser Thr Ser

<210> SEQ ID NO 15
<211> LENGTH: 23
<212> TYPE: PRT
<213> ORGANISM: Artificial Sequence
<220> FEATURE:
<223> OTHER INFORMATION: Synthetic Construct

<400> SEQUENCE: 15

Asp Val Val Met Thr Gln Thr Pro Leu Ser Leu Pro Val Ser Leu Gly
1 5 10 15

Asp Gln Ala Ser Ile Ser Cys
20

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Arg Ser Ser Gln Ser Leu Val His Ser Asn Gly Asn Thr Tyr Leu His
1 5 10 15

<210> SEQ ID NO 17
<211> LENGTH: 15
<212> TYPE: PRT

<213> ORGANISM: Artificial Sequence
<220> FEATURE:
<223> OTHER INFORMATION: Synthetic Construct

<400> SEQUENCE: 17

Trp Phe Leu Gln Lys Pro Gly Gln Ser Pro Lys Leu Leu Ile Tyr
1 5 10 15

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Lys Val Ser Asn Arg Phe Ser
1 5

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Gly Val Pro Asp Arg Phe Ser Gly Ser Gly Ser Gly Thr Asp Phe Thr
1 5 10 15

Leu Lys Ile Ser Arg Val Glu Ala Glu Asp Leu Gly Val Tyr Phe Cys
20 25 30

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Ser Gln Ser Thr His Phe Pro Trp Thr
1 5

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Phe Gly Gly Gly Thr Lys Leu Glu Ile Lys
1 5 10

<210> SEQ ID NO 22
<211> LENGTH: 408
<212> TYPE: DNA
<213> ORGANISM: Artificial Sequence
<220> FEATURE:
<223> OTHER INFORMATION: Synthetic Construct

<400> SEQUENCE: 22
atggattggc tgtggaactt gctattcctg atggcagctg cccaaagtat ccaagcacag 60
atccagttgg tgcagtctgg acctgagctg aagaagcctg gagagacagt caagatctcc 120
tgcaaggctt ctggatatat cttcacaaac tatggaatga actgggtgaa gcaggctcca 180

-continued

```
ggaaagaatt taaagtggat gggctggata aacaccaaca ctggagagcc aacatatgct    240

gaagagttca agggacggtt tgccttctct ttggaaacct ctgccagtat tgcctatttg    300

aagatcaaca acctcaaaaa tgaggacacg gctacatatt tctgttcaag agggggatta    360

ctaccacttt cttattgggg ccaagggact ctggtcactg tctctgca                 408


<210> SEQ ID NO 23
<211> LENGTH: 393
<212> TYPE: DNA
<213> ORGANISM: Artificial Sequence
<220> FEATURE:
<223> OTHER INFORMATION: Synthetic Construct

<400> SEQUENCE: 23

atgaagttgc ctgttaggct gttggtgctg atgttctgga ttcctgcttc caccagtgat     60

gttgtgatga cccaaactcc actctccctg cctgtcagtc ttggagatca agcctccatc    120

tcttgcagat ctagtcagag ccttgtacac agtaatggaa acacctattt acattggttc    180

ctgcagaagc caggccagtc tccaaagctc ctgatctaca aggtttccaa ccgattttct    240

ggggtcccag acaggttcag tggcagtgga tcagggacag atttcacact caagatcagc    300

agagtggagg ctgaggatct gggagtttat ttctgctctc aaagtacaca ttttccgtgg    360

acgttcggtg gaggcaccaa gctggaaatc aaa                                 393
```

MONOCLONAL ANTIBODY AND POLYCLONAL ANTIBODY AND OXYTOCIN QUANTIFICATION METHOD BASED ON SAME

CROSS-REFERENCE TO RELATED APPLICATIONS

This application is filed under the provisions of 35 U.S.C. § 371 and claims the priority of International Patent Application No. PCT/ES2021/070221, filed on 30 Mar. 2021 entitled "MONOCLONAL ANTIBODY AND POLYCLONAL ANTIBODY AND OXYTOCIN QUANTIFICATION METHOD BASED ON SAME" in the name of José Joaquín CERÓN MADRIGAL, et al., which claims priority to Spanish Patent Application No. P202030265 filed on 1 Apr. 2020, both of which are hereby incorporated by reference herein in their entirety.

SEQUENCE LISTING

The text of the computer readable sequence listing filed herewith, titled "41286.251_sequence_listing.ST25.txt," created Sep. 30, 2022, having a file size of 10,826 bytes, is hereby incorporated by reference in its entirety.

TECHNICAL FIELD OF THE INVENTION

The present invention relates to immunological assays for the detection of hormones in biological material. In particular, the present invention relates to immunological assays involving monoclonal and/or polyclonal antibodies and in which oxytocin is detected in biological material.

BACKGROUND OF THE INVENTION

Oxytocin is a hormone that is produced in the supraoptic and paraventricular nuclei of the hypothalamus and released into the circulatory system. Oxytocin is a hormone associated with the regulation of reproductive physiology events, such as childbirth and breastfeeding. In recent years, however, special importance has been given to its relationship with other different fields such as psychology and behaviour in both females and males. Oxytocin induces a decrease in cortisol levels, which reduces stress in both humans and animals. In general, oxytocin levels are measured in animals and humans to detect increases in plasma concentration indicative of a welfare and stress reduction situation. It is important to measure oxytocin levels to detect stressful states, which are harmful to health. Stressful states cause, among other effects, a reduction in the function of the immune system and predisposition to diseases. This deterioration of animal health and welfare is important in raised or farmed animals whose meat or other products derived therefrom, such as milk, will be used. The health and animal welfare of these livestock, in particular of pigs, becomes particularly important during the pregnancies of the females and after childbirth, affecting, for example, the care and survival of the offspring themselves.

Generally, the concentration of oxytocin has been measured by procedures that include an extraction or concentration of the sample by lyophilization. Oxytocin values in biological samples are generally very low. Both the extraction and the concentration of the sample aim to achieve sufficiently high values of oxytocin so that they can be measured.

The methods described in the prior art do not allow measuring all the oxytocin bound to proteins and, therefore, it is necessary in such methods to break the bonds between oxytocin and proteins. Reduction/alkylation (R/A) treatments are generally used for this purpose.

The application of R/A treatments to plasma samples results in oxytocin values several orders higher compared to the values in samples to which such treatments have not been applied (Brandtzaeg et al., 2016).

The methods used for extraction, lyophilization sample concentration, and reduction/alkylation treatments are technically complex and require several hours to perform, not being routinely used in analyses carried out on farm animals due to the long time they need. In addition, expensive reagents and laboratory materials are used in these processes, resulting in high analysis prices.

MacLean et al. measured oxytocin in dog saliva by various techniques, such as high performance liquid chromatography coupled to mass spectrometry (HPLC-MS) and Cayman Chemical and Arbor Assays commercial enzyme-linked immunoabsorption assays (ELISA), which do not use reduction and alkylation treatments (MacLean et al., 2018). This document, however, does not describe any assay in which free oxytocin and protein-bound oxytocin can be specifically quantified, nor does it describe the use of antibodies with such specificity against free oxytocin and protein-bound oxytocin.

Recently, a method for measuring oxytocin in sow saliva samples, at different times after delivery, in which oxytocin concentration was measured, was described with an AlphaLISA® assay using monoclonal antibody-coated spheres (López-Arjona et al., 2020). This document does not describe any assays in which free oxytocin and protein-bound oxytocin can be specifically quantified. It also does not describe the use of antibodies with specificity against free oxytocin and protein-bound oxytocin.

There is a need in the art to develop a method for measuring both free oxytocin and protein-bound oxytocin.

DESCRIPTION OF THE INVENTION

In the present specification, the oxytocin is from mammals. Preferably, said mammals are selected from the group consisting of pigs, dogs, equines (comprising horses, mules and donkeys) and humans. More preferably, the oxytocin consists of the sequence SEQ ID NO: 1.

Herein, the term "sample" refers to a sample of a body fluid; to a sample of cells; to a sample of a tissue, or of an organ; or to a wash/rinse fluid sample obtained from an external or internal body surface. Samples can be obtained by well-known techniques. More preferably, the samples are samples of body fluids, e.g., preferably, blood, plasma, serum, urine, saliva, tears, and fluids obtainable from the mammary glands, e.g., milk. More preferably, the samples of body fluid are free of cells from the animal or subject. Tissue or organ samples may be obtained from any tissue or organ by, for example, a biopsy. Cells may be obtained or separated from body fluids or tissues or organs by techniques such as filtration, centrifugation, or cell sorting. Preferably, the samples of cells, tissues or organs are obtained from body fluids, cells, tissues or organs known or suspected to contain oxytocin. More preferably, the samples are samples of serum, plasma, saliva, urine, and cerebrospinal fluid.

Saliva has advantages compared to other types of sample, as it can be obtained in a simple way, without producing stress or pain. For this reason, saliva samples are increasingly used for the determination of biomarkers of stress or well-being in animals, preferably in pigs.

In the present patent, “free oxytocin” refers to what a person skilled in the art would understand by said term, which consists of oxytocin that is in free form, i.e., not bound to proteins, under physiological conditions.

An exemplary antibody is composed of two pairs of polypeptide chains. Each pair of polypeptide chains has a light chain (about 25 kD) and a heavy chain (about 50-70 kD). The N-terminal domain of each chain defines a variable region of about 100 to 110 or more amino acids responsible for antigen recognition. The light chain variable domain is also referred to as the “variable light chain” or “VL” and the heavy chain variable domain is also referred to as the “variable heavy chain” or “VH”.

Herein, “CDR” or “complementarity determining region” refers to an amino acid sequence found in the variable domains of antibodies that gives antibodies their specificity for the antigen.

Herein, the term “ELISA” refers to enzyme-linked immunosorbent assay, which is an immunoassay technique in which an immobilized antigen is detected by an antibody bound to an enzyme (peroxidase, alkaline phosphatase, etc.,) capable of generating a detectable product from a substrate by a colour change or some other type of change caused by the enzymatic action on said substrate. In said technique, there may be a primary antibody that recognizes the antigen and that in turn is recognized by a secondary antibody bound to said enzyme. The antigen can be detected indirectly in the sample by colour changes measured by spectrophotometry.

The present invention provides an in vitro method for the quantification of free oxytocin, protein-bound oxytocin able to be released in a reduction/alkylation treatment, and protein-bound oxytocin, in a sample, without carrying out a reduction/alkylation treatment, wherein said method comprises:

(a) carrying out a first assay comprising:
  - adding to said sample a monoclonal antibody that specifically binds to free oxytocin and protein-bound oxytocin able to be released in a reduction/alkylation treatment, wherein said monoclonal antibody comprises:
    - a heavy chain CDR1 region consisting of the sequence SEQ ID NO: 6;
    - a heavy chain CDR2 region consisting of the sequence SEQ ID NO: 8.
    - a heavy chain CDR3 region consisting of the sequence SEQ ID NO: 10;
    - a light chain CDR1 region consisting of the sequence SEQ ID NO: 16;
    - a light chain CDR2 region consisting of the sequence SEQ ID NO: 18; and
    - a light chain CDR3 region consisting of the sequence SEQ ID NO: 20;
  - determining the amount or concentration of monoclonal antibody bound to free oxytocin and protein-bound oxytocin able to be released in a reduction/alkylation treatment; and
  - determining the amount or concentration of free oxytocin and protein-bound oxytocin able to be released in a reduction/alkylation treatment from the amount or concentration of monoclonal antibody bound to free oxytocin and to protein-bound oxytocin able to be released in a reduction/alkylation treatment;

(b) carrying out a second test, simultaneously or sequentially, in any order, comprising:
  - adding to said sample a polyclonal antibody that specifically binds to protein-bound oxytocin;
  - determining the amount or concentration of polyclonal antibody bound to protein-bound oxytocin; and
  - determining the amount or concentration of protein-bound oxytocin from the amount or concentration of polyclonal antibody bound to protein-bound oxytocin.

In a preferred embodiment of the method of the invention, said protein-bound oxytocin is albumin-bound oxytocin.

In a preferred embodiment, the method of the invention further comprises:

(c) adding the free oxytocin amount or concentration value obtained in step (a) to the protein-bound oxytocin amount or concentration value obtained in step (b).

In another preferred embodiment, the method of the invention further comprises:

(c) carrying out a mathematical operation between the free oxytocin amount or concentration value obtained in step (a) and the protein-bound oxytocin amount or concentration value obtained in step (b), such as division or multiplication.

The method of the invention avoids having to carry out a reduction/alkylation (R/A) procedure to determine the free oxytocin, this being one of the main technical differences with respect to the state of the art, which makes the quantification of oxytocin in the method of the invention cheaper and faster than other procedures. Accordingly, the method of the invention differs from the methods described in the prior art in that it can be done in less time and with less material means. The method of the invention, in addition to being able to be implemented in any laboratory, is especially indicated to be carried out in an ambulatory mode, in situ, in the animal farms.

The monoclonal antibody and the polyclonal antibody have different specificities. Such differences in specificity result from the different method of producing such antibodies. Oxytocin-KLH has been used for immunizations and oxytocin-BSA has been used to purify the monoclonal and polyclonal antibody. However, in the monoclonal antibody production method a cell fusion, a hybridoma, is used, while in the polyclonal antibody production procedure a direct inoculation of oxytocin-KLH in a rabbit is used, thereby causing the rabbit to produce antibodies. Therefore, due to differences in the production procedure, the antibodies have different specificities.

In one embodiment of the method of the invention, the variable domain of the heavy chain VH has at least 95%, 96%, 97%, 98%, or 99% identity to the sequence SEQ ID NO: 3 and the variable domain of the light chain VL has at least 95%, 96%, 97%, 98%, or 99% identity to the sequence SEQ ID NO: 13.

In one embodiment of the method of the invention, the variable domain of the heavy chain VH consists of the sequence SEQ ID NO: 3 and the variable domain of the light chain VL consists of the sequence SEQ ID NO: 13.

In one embodiment of the method of the invention, it is not necessary to subject the samples to any pre-processing.

If the samples are frozen, said samples are thawed at room temperature prior to application of the method of the invention.

In a preferred embodiment of the method of the invention, the monoclonal antibody and/or the polyclonal antibody are added at a concentration in the range 10-20 nM.

In another preferred embodiment of the method of the invention, the incubation time of the monoclonal antibody and/or the polyclonal antibody with the sample is between 1 and 2 hours.

In one embodiment of the method of the invention, the signal emitted by oxytocin from the sample is detected by binding to the monoclonal antibody and/or the polyclonal antibody. Such a signal may be an absorbance or fluorescence signal and may be detected by methods known in the state of the art, for example, in absorbance or fluorescence readers. The signal emitted by each antibody may be the same or different. The amount or concentration of oxytocin is determined, by methods known in the state of the art, from the value of said signal.

The method of the invention offers the following advantages:

(a) It allows to determine different types of oxytocin (free oxytocin, protein-bound oxytocin able to be released in a reduction/alkylation treatment and protein-bound oxytocin), without subjecting the sample to any R/A treatment prior to measurement, whereas in traditional methods it is necessary to subject the sample to a R/A treatment prior to measurement.

(b) It manages to measure, using the same analytical system, different types of oxytocin simultaneously or serially and in any order (first the free oxytocin and the protein-bound oxytocin able to be released in a reduction/alkylation treatment and, then, the protein-bound oxytocin, or vice versa, in the opposite order, first the protein-bound oxytocin and, then, the free oxytocin and the protein-bound oxytocin able to be released in a reduction/alkylation treatment), which makes possible important savings of time and also of materials, therefore being more economical from a commercial point of view. Simultaneous measurement can be carried out by binding each antibody to a different marker and using the same steps described above.

The method of the invention has been functionally tested by carrying out analytical validation tests. The method of the invention presents an imprecision, intra-assay and inter-assay, of less than 15%, is linear, presents percentages of oxytocin recovery between 80 and 120%, and the limit of detection and quantification allows measuring the concentrations of free oxytocin and protein-bound oxytocin that are normally present in biological samples. The correlation of the oxytocin values quantified with the assay with the monoclonal antibody of the invention and those quantified with the commercial ELISA kit of Cayman Chemical, which is used to measure free oxytocin with a pre-processing by R/A, was greater than 0.9, indicating that the values of the two methods have a high correlation.

In the method of the invention, the first and second assays (with the monoclonal antibody and the polyclonal antibody, or vice versa) are selected from the group consisting of immunofluorescence, immunohistochemistry, immunochromatography, luminescence, homogeneous amplified luminescent proximity assay, immunoelectrotransfer, ELISA, western blot, nephelometry, immunoturbidimetry, lateral chromatography, and microarrays.

In the method of the invention, the first and second assays (with the monoclonal antibody and the polyclonal antibody, or vice versa) are carried out simultaneously or sequentially.

In the method of the invention, the first and second assays (with the monoclonal antibody and the polyclonal antibody, or vice versa) are carried out in any order.

In the method of the invention, said monoclonal antibody and/or said polyclonal antibody are attached to a labelling probe or to a sphere attached to a labelling probe. Said labelling probes may be the same or different for each monoclonal or polyclonal antibody.

In the method of the invention, said labelling probe is selected from the group consisting of a fluorophore, a chromophore, a bioluminescent probe, a radioactive probe, an enzyme and colloidal gold.

In the method of the invention, the sample used to measure its total oxytocin content is selected from the group consisting of serum, plasma, saliva, urine, and cerebrospinal fluid.

The present invention also provides a monoclonal antibody that specifically binds to free oxytocin and protein-bound oxytocin able to be released in a reduction/alkylation treatment, wherein said monoclonal antibody comprises:

a heavy chain CDR1 region consisting of the sequence SEQ ID NO: 6;

a heavy chain CDR2 region consisting of the sequence SEQ ID NO: 8;

a heavy chain CDR3 region consisting of the sequence SEQ ID NO: 10;

a light chain CDR1 region consisting of the sequence SEQ ID NO: 16;

a light chain CDR2 region consisting of the sequence SEQ ID NO: 18; and a light chain CDR3 region consisting of the sequence SEQ ID NO: 20.

In one embodiment of the monoclonal antibody of the invention, the variable domain of the heavy chain VH has at least 95% identity to the sequence SEQ ID NO: 3 and the variable domain of the light chain VL has at least 95% identity to the sequence SEQ ID NO: 13.

In one embodiment of the monoclonal antibody of the invention, the variable domain of the heavy chain VH consists of the sequence SEQ ID NO: 3 and the variable domain of the light chain VL consists of the sequence SEQ ID NO: 13.

The present invention also provides a polynucleotide encoding the monoclonal antibody of the invention, comprising the sequence SEQ ID NO: 22, which encodes the variable domain of the heavy chain, and sequence SEQ ID NO: 23, which encodes the variable domain of the light chain.

The present invention also provides the use of a polynucleotide that comprises the sequence SEQ ID NO: 22, which encodes the variable domain of the heavy chain, and sequence SEQ ID NO: 23, which encodes the variable domain of the light chain, in the production of the monoclonal antibody of the invention.

The present invention also provides a polyclonal antibody that specifically binds to protein-bound oxytocin.

The monoclonal antibody and/or polyclonal antibody of the invention are attached to a labelling probe or to a sphere attached to a labelling probe.

Said labelling probe attached to the monoclonal antibody and/or polyclonal antibody of the invention is selected from the group consisting of a fluorophore, a chromophore, a bioluminescent probe, a radioactive probe, an enzyme and colloidal gold. Said labelling probes may be the same or different for each monoclonal or polyclonal antibody.

The present invention also provides a composition comprising the monoclonal antibody and/or the polyclonal antibody of the invention.

The present invention also provides the use of such a composition comprising the monoclonal antibody of the invention and/or the polyclonal antibody of the invention, in the in vitro detection of free oxytocin and protein-bound oxytocin able to be released in a reduction/alkylation treatment and/or of protein-bound oxytocin in a sample.

The present invention also provides a kit for detecting free oxytocin and protein-bound oxytocin able to be released in a reduction/alkylation treatment and/or of protein-bound oxytocin in a sample, wherein said kit comprises:

(i) the monoclonal antibody and/or the polyclonal antibody or the composition of the invention comprising each of the monoclonal and polyclonal antibodies, or the combination of both; and (ii) buffer solutions to carry out a reaction to form a complex between the monoclonal antibody and free oxytocin and protein-bound oxytocin able to be released in a reduction/alkylation treatment and/or between the polyclonal antibody and protein-bound oxytocin.

In the kit of the invention, said monoclonal antibody and/or polyclonal antibody are attached to a labelling probe or to a sphere attached to a labelling probe.

In the kit of the invention, said labelling probe is selected from the group consisting of a fluorophore, a chromophore, a bioluminescent probe, a radioactive probe, an enzyme and colloidal gold. Said labelling probes may be the same or different for each monoclonal or polyclonal antibody.

The kit of the invention further comprises reagents for carrying out the reaction to form such complexes between the monoclonal antibody and the free oxytocin and/or the polyclonal antibody and the protein-bound oxytocin and for carrying out the detection of such complexes.

The kit may integrate in a single device both antibodies, monoclonal and polyclonal, or the compositions containing each antibody, monoclonal and polyclonal, or comprise separate devices for each antibody or for each composition containing each antibody, to carry out each assay (a) or (b) of the method of the invention and both separate devices to be presented together in a single package or presentation, or to be presented separately, each in its own package or presentation.

The kit of the invention is used on a sample selected from the group consisting of serum, plasma, saliva, urine, and cerebrospinal fluid.

The kit of the invention can be used in any biological sample that may have oxytocin.

Additionally, the present invention provides the use of the monoclonal antibody of the invention in the in vitro detection in a sample of free oxytocin and protein-bound oxytocin able to be released in a reduction/alkylation treatment.

Preferably, said sample in which the monoclonal antibody of the invention is used contains free oxytocin and protein-bound oxytocin.

Additionally, the present invention also provides the use of the polyclonal antibody of the invention in the in vitro detection of protein-bound oxytocin in a sample.

Preferably, said sample in which the polyclonal antibody of the invention is used contains free oxytocin and protein-bound oxytocin.

In a preferred embodiment, said monoclonal antibody and/or said polyclonal antibody are used attached to a labelling probe.

Said labelling probe is selected from the group consisting of a fluorophore, a chromophore, a bioluminescent probe, a radioactive probe, an enzyme and colloidal gold. The labelling probes may be the same or different for each antibody, monoclonal or polyclonal.

One embodiment of the invention relates to the use of the kit of the invention in the in vitro detection, in a sample, of free oxytocin and protein-bound oxytocin able to be released in a reduction/alkylation treatment and/or protein-bound oxytocin.

DESCRIPTION OF EMBODIMENTS

Materials and Methods

Animals and Samples

Figure 1:
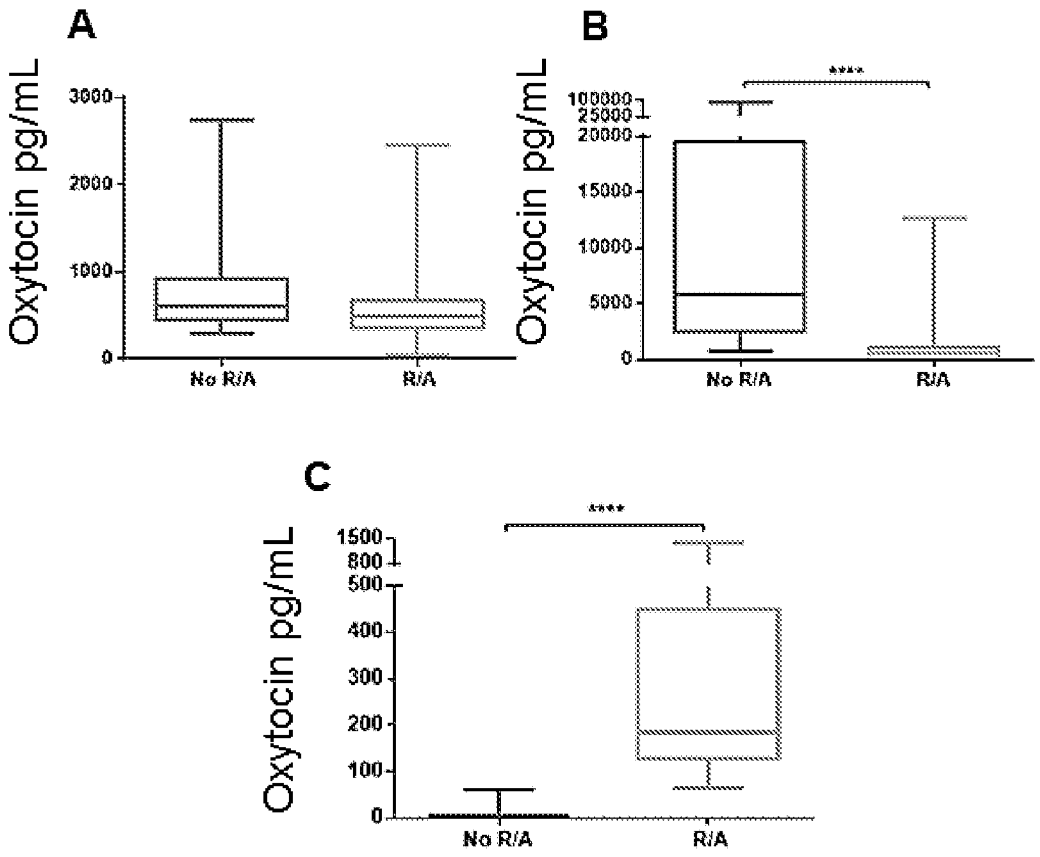
FIG. 1. Results of the concentrations of oxytocin in the saliva of pigs before (No R/A) and after (R/A) treatment of the saliva samples with the AlphaLISA® assay using the monoclonal antibody of the invention "P26C" (A), the AlphaLISA® assay using the polyclonal antibody of the invention "PO-10" (B) and the assay with the ELISA kit of Cayman Chemical (C). The asterisks indicate significant differences (****P≤0.0001).

The samples used in this study were obtained from 10 female pigs (*Sus scrofa domesticus*), Large White. The pigs had ad libitum access to a balanced diet and water, with a temperature between 19-23° C. and samples were taken between 8:30 and 10:00 h. A sample of each pig was taken 3 times during the study: day 58 of gestation, day 7 after farrowing (during lactation) and day 45 after farrowing. The animals were housed in the experimental farm of the University of Murcia (Murcia, Spain), in groups with a minimum space of 1.64 $m^2$ per animal on day 58 of gestation and individually on days 7 and 45 after delivery (recommendations described in Directive 2001/88/EC, 2001 and Directive 2001/93/EC, 2001).

Saliva samples were collected using Salivette tubes (Sarstedt, Aktiengesellschaft & Co.) containing a sponge. The pigs were allowed to chew the sponge, which was attached to a thin, flexible metal rod, until it was completely wet (or at least 1 minute). The sponges were then placed into the Salivette tubes which were immediately centrifuged at 3000 g for 10 minutes at 4° C. The saliva was then transferred into 1.5 mL tubes and stored at −80° C. until analysis. In all cases, at least 500 microliters of saliva were obtained.

All procedures were approved by the Ethics Committee of the University of Murcia.

Reduction/Alkylation Procedure (R/A)

The R/A procedure was carried out following the protocol described in Brandtzaeg et al. (2016). 30 samples of pig saliva were treated. 100 μl of each sample was diluted in 200 μl 50 mM Tris-HCl buffer (pH 8.0). Then, 5 μl of 0.5 M dithiothreitol (DTT) (GE Healthcare Life Sciences) was added to 100 μl of the diluted saliva sample, mixed for 30 seconds and incubated at 37° C. for 45 minutes, followed by cooling to room temperature (22° C.). Next, 15 μL of 0.5 M iodoacetamide (IAM) (GE Healthcare Life Sciences) was added to each solution, mixed for 30 seconds and incubated at 22° C. in darkness for 20 minutes. Then, 80% acetonitrile (ACN) solution (Scharlab, SL), in ultrapure water (Millipore) (v/V), previously kept on ice, was added, mixed for 30 seconds and centrifuged for 15 minutes at 14,000 rpm in an Eppendorf Sorvall ST 8R centrifuge (Thermo Fisher Scientific). After centrifugation, the supernatant was pipetted into a new Eppendorf tube and evaporated to dryness in a Speed Vac concentrator (Eppendorf Concentrator 5301) followed by reconstitution in 100 μL saline phosphate buffer (PBS). The treated samples were diluted 1:2 with each buffer corresponding to each assay.

To assess whether the R/A procedure could affect the assays used in our study regardless of the effect it has on bound oxytocin, the assay buffer used for each assay was processed using the R/A protocol and analysed as an unknown sample in each of the three assays of our study.

Example 1. Production of the Monoclonal Antibody of the Invention "P26C" which Specifically Recognizes Free Oxytocin

Generation of Hybridoma 3 mice (BALB/c) were immunized with two intraperitoneal injections separated by an interval of 15 days with 50 μg of oxytocin-KLH (Cusabio) as antigen, where KLH is Keyhole Limpet Haemocyanin, that is, the haemocyanin of the keyhole limpet (*Megathura crenulata*). The antigen was emulsified with Freund's complete adjuvant (CCF, Sigma F-5881) at the first injection, and with Freund's incomplete adjuvant (CIF. Sigma F-5506) for the second intraperitoneal injection. The final immunization consisted of an intravenous or intra-splenic injection of 50 μg of antigen without the adjuvant.

Three days later, the spleen was extracted from the mice and the cells were fused to the Sp2/0-Ag14 murine myeloma cell line, developed from non-immunoglobulin-secreting BALB/c mice using 50% solution polyethylene glycol (Sigma). Hybridomas were selected by growth in RPMI 1640 medium (Biowhitaker) containing hypoxanthine, aminopterin, and thymidine (HAT), which was supplemented with 10% fetal bovine serum (Gibco), 2 mM glutamine (Gibco), 1 mM pyruvate (Sigma), and 1% penicillin/streptomycin (Gibco). In the HAT medium with aminopterin, only hybrid cells, consisting of B cells and myeloma cells, grow because B cells possess the entire panel of DNA synthesis rescue pathway enzymes and, therefore, can use the hypoxanthine and thymidine from the medium.

Finally, hybridoma supernatants were analysed by ELISA assay for the presence of anti-oxytocin immunoglobulin-secreting hybridomas. Positive hybridomas were cloned by limit dilution and expanded and frozen in liquid nitrogen.

Identification of the Monoclonal Antibody

An analysis of the supernatants of the hybridomas generated by indirect ELISA assay using Oxytocin-BSA was carried out. To this end, they were incubated in 96-well flat-bottomed Nunc microplates (Maxisorp), with 50 μL of oxytocin-BSA (250 ng antigen per well) in carbonate-bicarbonate buffer pH 9.8 overnight, at 4° C., to allow the correct adhesion of the proteins to the plate. Subsequently the plates were washed with 100 μL 0.05% PBS/Tween 20 and blocked for 30 minutes at 37° C. with 100 μL phosphate buffered saline (PBS) with 5% milk powder. The plates were then incubated 1 hour at 37° C., with 100 μL per well of each supernatant from the hybridomas. Next, three washes were carried out with 0.1% PBS/Tween 20 buffer. Then, 100 μL per well of a mouse anti-IgG antibody conjugated with horseradish peroxidase was added at a 1:2500 dilution and incubated for 1 hour at room temperature. After 5 washes with 0.1% PBS/Tween 20 buffer, to remove all labelled molecules not fixed in the form of immunocomplexes, the enzymatic substrate in solution (0.1 M sodium citrate, 0.1 M citric acid, 2,2'-azino-bis(3-ethylbenzothiazoline-6-sulfonic acid) (ABTS) and $H_2O_2$) was added. Subsequently, absorbance (OD) was measured on a spectrophotometer (BioTek) at a wavelength of 405 nm every 5 minutes to a total of 25 minutes.

The specific anti-oxytocin antibody was identified in the P26C hybridoma supernatant in said indirect ELISA assay using oxytocin-BSA. Clone P26C was selected because the highest absorbance signal was obtained with said clone in said ELISA assay, indicating a higher affinity for oxytocin than the other clones.

A dot-blot assay was carried out with clone P26C, which determined that it had reactivity against oxytocin of a high number of species, such as pig, dog, horse and human oxytocin.

Purification of the Monoclonal Antibody P26C

For purification of the P26C monoclonal antibody from the supernatant obtained from the selected hybridoma, a HiTrap™ Protein G HP affinity column (GE Healthcare Life Sciences) was used using a ÄKTA pure chromatography system (GE Healthcare Life Sciences).

Structural Characterisation of the Monoclonal Antibody P26C

Total RNA was extracted from hybridoma cells and the cDNA was subsequently synthesized. The monoclonal antibody variable domains were then amplified by isotype-specific PCR, subcloned into a separate standard cloning vector, and sequenced. The isotype of the monoclonal antibody was determined to be IgGκ. The variable domains of 5 clones were sequenced and the sequence was found to be identical in all 5 clones. Table 1 shows the sequence details of monoclonal antibody P26C.

TABLE 1

| Fragment/Region/Sequence | SEQ ID NO |
|---|---|
| Variable domain of the heavy chain VH including signal peptide | SEQ ID NO: 2 |
| Variable domain of the heavy chain VH | SEQ ID NO: 3 |
| Signal peptide of the heavy chain VH | SEQ ID NO: 4 |
| FR1 framework region of the heavy chain VH | SEQ ID NO: 5 |
| CDR1 region of the heavy chain VH | SEQ ID NO: 6 |
| FR2 framework region of the heavy chain VH | SEQ ID NO: 7 |
| CDR2 region of the heavy chain VH | SEQ ID NO: 8 |
| FR3 framework region of the heavy chain VH | SEQ ID NO: 9 |
| CDR3 region of the heavy chain VH | SEQ ID NO: 10 |
| FR4 framework region of the heavy chain VH | SEQ ID NO: 11 |
| Variable domain of the light chain VL including signal peptide | SEQ ID NO: 12 |
| Variable domain of the light chain VL | SEQ ID NO: 13 |
| Signal peptide of the light chain VL | SEQ ID NO: 14 |
| FR1 framework region of the light chain VL | SEQ ID NO: 15 |
| CDR1 region of the light chain VL | SEQ ID NO: 16 |
| FR2 framework region of the light chain VL | SEQ ID NO: 17 |
| CDR2 region of the light chain VL | SEQ ID NO: 18 |
| FR3 framework region of the light chain VL | SEQ ID NO: 19 |
| CDR3 region of the light chain VL | SEQ ID NO: 20 |
| FR4 framework region of the light chain VL | SEQ ID NO: 21 |

TABLE 1-continued

| Fragment/Region/Sequence | SEQ ID NO |
|---|---|
| Nucleotide sequence encoding the variable fragment of the heavy chain VH including signal peptide | SEQ ID NO: 22 |
| Nucleotide sequence encoding the variable fragment of the light chain VL including signal peptide | SEQ ID NO: 23 |

Example 2. Determination of Free Oxytocin Concentrations in Saliva Samples

The saliva samples described in Materials and Methods were thawed at room temperature and 10 μL of 1:2 sample was diluted in assay buffer (AlphaLISA® Universal buffer, Perkin elmer, Inc.). An AlphaLISA® assay (Perkin Elmer, Inc.) was carried out, in 96-well plates, with a reaction volume of 50 μL per well, using spheres coated with the monoclonal antibody P26C and oxytocin concentrations in the samples were determined.

Example 3. Production of the Polyclonal Antibody of the Invention "PO-10" that Specifically Recognizes Protein-Bound Oxytocin A New Zealand rabbit (female, 2.5 kg, 3 months of age) was immunized with an oxytocin-KLH (Cusabio) conjugate as antigen, using 150 μg mixed in Freund's complete adjuvant for the first injection and Freund's incomplete adjuvant for the second and subsequent injections. One week after each immunization, several blood samples were collected and an ELISA assay was carried out to evaluate antibody titre using oxytocin-BSA-coated plates and a horseradish peroxidase-labelled rabbit anti-IgG secondary antibody.

Purification of Polyclonal Antibody

An N-hydroxysuccinimide (NHS)-activated HiTrap™ HP (GE Healthcare Life Sciences) affinity column was used, to which oxytocin-BSA (Cusabio) was coupled and 1 mL batches of rabbit oxytocin antiserum were passed through the column using a ÄKTA pure chromatography system (GE Healthcare Life Sciences).

Example 4. Determination of Protein-Bound Oxytocin Concentrations in Saliva Samples The saliva samples described in the Materials and Methods section were thawed at room temperature and 10 μL of sample was diluted in assay buffer (AlphaLISA® immunoassay buffer, Perkin Elmer Inc.). An AlphaLISA® (Perkin Elmer, Inc.) indirect competition assay was carried out on 96-well plates, with a final reaction volume of 50 μL per well, using G-protein coated beads (Perkin Elmer Inc.) and oxytocin concentrations in the samples were determined. Different concentrations of biotinylated oxytocin (0-6 nM) and the polyclonal antibody of the invention PO-10 (10-20 nM) were assayed. Different concentrations of donor beads (Perkin Elmer Inc.) and G-protein coated acceptor beads were used at concentrations between 20-40 μg/mL.

Example 5. Measurement of Oxytocin by the Method of the Invention. Comparative Assay with Cayman Chemical ELISA Kit Imprecision was calculated as variations between assays and intra-assays and expressed as coefficients of variation (CV). Five replicates of each sample (low, medium and high saliva samples) were analysed at the same time, to determine the intra-assay precision of the method. Five aliquots of each saliva sample were stored in plastic vials at −80° C. until analysis. On the day of analysis, samples were brought to room temperature prior to oxytocin measurement. These samples were measured in duplicate five times over five different days to determine accuracy between assays using freshly prepared calibration curves.

Accuracy was assessed by evaluating linearity after dilution and recovery experiments. For the linearity evaluation, two samples with high and medium oxytocin values were diluted in series. Dilutions were 1:4 to 1:128 and 1:2 to 1:64 with assay buffer (AlphaLISA® immunoassay buffer, Perkin Elmer Inc.) for the high and medium value sample, respectively. For the recovery test, a pig saliva sample with a known oxytocin concentration with different amounts of oxytocin standard (120, 80, 40, 20 and 10 ng/L) was diluted (1:2). The percentages of oxytocin concentrations measured at the expected oxytocin concentrations were then calculated.

The limit of detection (LD) was calculated from 12 replicate oxytocin assay buffer determinations (AlphaLISA® immunoassay buffer, Perkin Elmer Inc.) as mean value plus 3 standard deviations (SD). The Lower Limit of Quantification (LLOQ) was calculated based on the lowest oxytocin concentration that could be measured with 20% accuracy. For this, a saliva sample was serially diluted with assay buffer and analysed five times at the same time for each dilution.

A commercially available ELISA kit from Cayman Chemical was used for the measurement of oxytocin for comparative purposes within the validation.

Statistical Analysis

The data obtained from different days of gestation and lactation were evaluated to determine the normality of the distribution, using the Shapiro-Wilk test, which provides a non-parametric distribution. Results below the limit of detection were set at the limit of detection of each method. The values were logarithmically transformed and the paired t-test was used for the differences between before and after the R/A procedure within each method. A one-way repeated measures ANOVA was applied to the log-transformed values, followed by uncorrected Fisher's LSD to compare oxytocin values obtained at different times on day 58 before farrowing and days 7 and 45 after farrowing. Spearman's correlation coefficients were calculated to evaluate the correlation between the three methods before and after the R/A procedure (GraphPad prism 5.00 for Windows).

In the polyclonal antibody immunoassay, intra-assay coefficients of variation (CV) were in the range 4.36-11.37% and inter-assay coefficients of variation were in the range 8.52-13.38%. Dilution of saliva samples resulted in linear regression equations with a correlation coefficient ranging from 0.98 to 0.99. The beta coefficients were significantly non-zero and the run test showed no deviation from linearity. The recovery results obtained were between 80% and 116% and the limit of detection of the assay was 58.4 pg/mL.

In the assay with the Cayman Chemical commercial kit, the intra-assay coefficients of variation were in the range 11.34-15.72% and the inter-assay coefficients of variation were in the range 18.56-21.04%. Dilution of saliva samples resulted in linear regression equations with a correlation coefficient of 0.99. The beta coefficients were significantly different from zero and the run test showed no deviation from linearity and the limit of detection of the assay was 4.66 pg/mL.

Effects of R/A Treatment

The results obtained for the samples are shown in FIG. 1. In the AlphaLISA® assay with the monoclonal antibody, the oxytocin concentrations of the samples showed no significant differences (P=0.0634) between samples with R/A procedure (mean value of 702.9 pg/mL) and without R/A procedure (mean value of 882.1 pg/mL). In the AlphaLISA® assay with the polyclonal antibody, the oxytocin concentrations of the samples with the R/A procedure (mean value of 1308 pg/mL) were significantly lower (P<0.0001) than those obtained without the R/A procedure (mean value of 13492 pg/mL). Finally, in the assay with the Cayman Chemical commercial kit, oxytocin concentrations (P<0.0001) were significantly higher in samples with R/A procedure (mean value of 320.4 pg/mL) compared to those without R/A procedure (mean value of 11.8 pg/mL). Only 6 of a total of 30 samples without R/A procedure give results above the detection limit of this method and in samples below the detection limit the assay detection limit value was used for the statistical study.

When the buffers were analysed, the samples gave a result below the limit of detection before and after the R/A procedure in all three assays.

Biological Response of Each Assay

Figure 2:
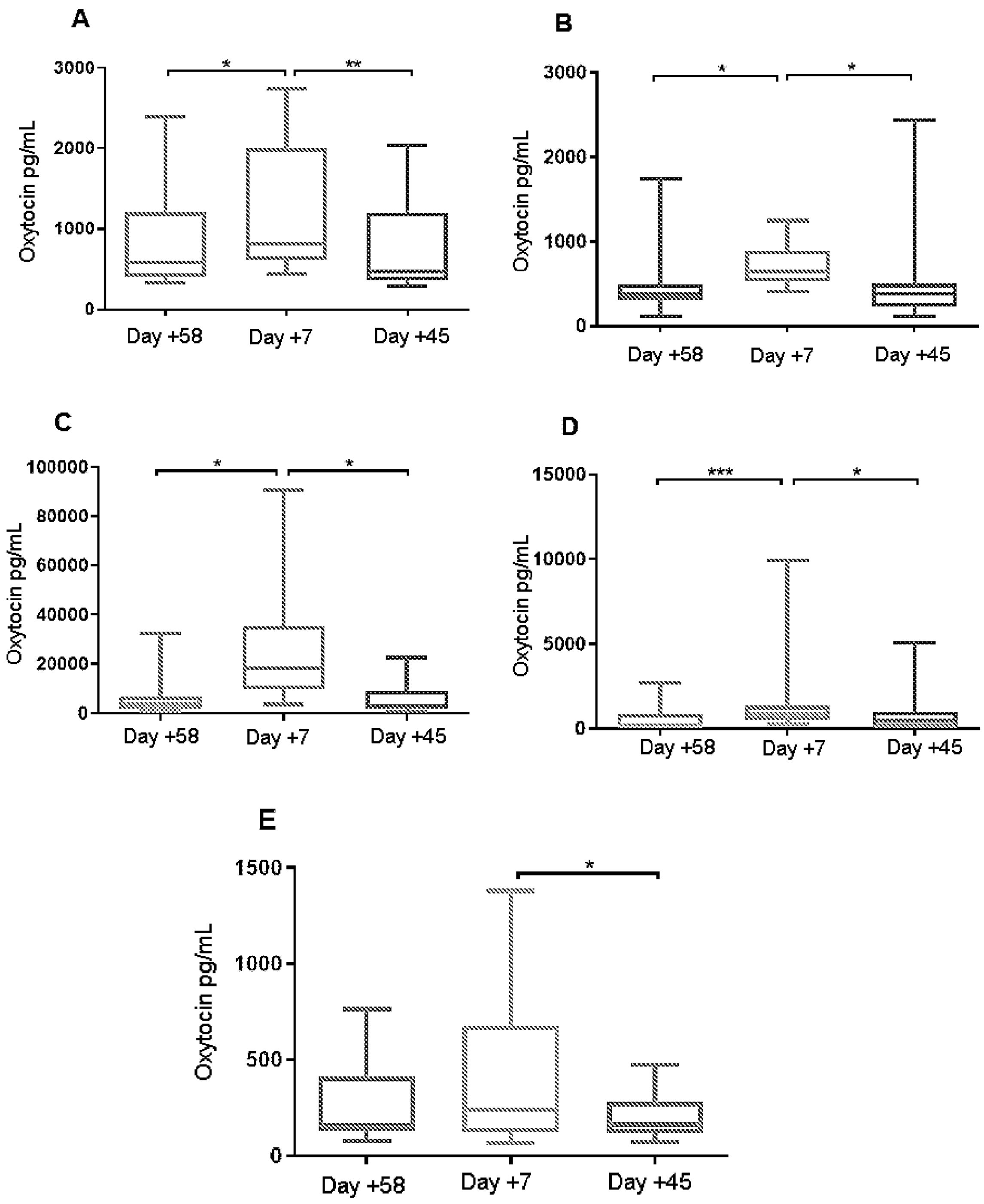
FIG. 2. Changes in oxytocin concentrations on different days before and after farrowing, in sows: day 58 of gestation (Day +58), day 7 after farrowing (Day +7) and day 45 after farrowing (Day +45) with the AlphaLISA® assay using the monoclonal antibody of the invention before (A) and after R/A treatment (B), the AlphaLISA® assay using the polyclonal antibody of the invention before (C) and after R/A treatment (D) and the ELISA assay with the Cayman Chemical kit after R/A treatment (E). The asterisks indicate significant differences (*P≤0.001 P≤0.01; *P≤0.05).

The biological response of oxytocin concentrations with each assay is shown in FIG. 2.

In the AlphaLISA® assay with the monoclonal antibody without R/A procedure, salivary oxytocin concentrations increased significantly on day 7 after farrowing, with a mean value of 1153 pg/mL, compared to gestation day 58 (mean value of 862 pg/mL) (1.34-fold; P=0.038) and day 45 after farrowing (mean value of 763 pg/mL) (1.51-fold; P=0.0038). When this method was applied with the R/A procedure, salivary oxytocin concentration increased significantly on day 7 after farrowing, with a mean value of 701.4 pg/mL, compared to day 58 gestation (mean value of 524.1 pg/mL) (1.34-fold; P=0.0159) and day 45 after farrowing (mean value of 552.1 pg/mL) (1.27-fold; P=0.0138).

In the AlphaLISA® assay with the polyclonal antibody without R/A procedure, salivary oxytocin concentrations increased significantly on day 7 after farrowing, with a mean value of 25695 pg/mL, compared to gestation day 58 (mean value of 6896 pg/mL) (3.72-fold; P=0.0007) and day 45 after farrowing (mean value of 5939 pg/mL) (4.33-fold; P=0.0001). When the R/A procedure was applied to this assay, salivary oxytocin concentrations increased significantly on day 7 after farrowing, with a mean value of 1677 pg/mL, compared to gestation day 58 (mean value of 534.8 pg/mL) (3.14-fold; P=0.0003) and day 45 after farrowing (mean value of 906.5 pg/mL) (1.85-fold; P=0.0157).

Finally, when the Cayman Chemical ELISA kit was used without the R/A procedure, only 6 of the analysed samples were above the detection limit, so it was not possible to apply these conditions to evaluate possible biological changes. In the ELISA assay with the Cayman Chemical kit, with R/A procedure, salivary oxytocin concentrations increased significantly on day 7 after farrowing, with a mean value of 448.6 pg/mL, compared to day 45 after farrowing (mean value of 208.8 pg/mL) (2.15-fold; P=0.039) but there were no significant differences with gestation day 58 (mean value of 275.5 pg/mL) (1.63-fold; P=0.1999).

The summary of correlations between procedures is shown in Table 2. The asterisks indicate the statistical significance (*P≤0.001; P≤0.01; *P≤0.05).

TABLE 2

| | AlphaLISA monoclonal no R/A | AlphaLISA monoclonal R/A | AlphaLISA polyclonal no R/A | AlphaLISA polyclonal R/A | Cayman kit no R/A | Cayman kit R/A |
|---|---|---|---|---|---|---|
| AlphaLISA monoclonal no R/A | | 0.65*** | 0.63*** | 0.39* | 0.51*** | 0.67*** |
| AlphaLISA monoclonal R/A | | | 0.68*** | 0.58*** | 0.47** | 0.53*** |
| AlphaLISA polyclonal no R/A | | | | 0.48** | 0.25 | 0.44** |
| AlphaLISA polyclonal R/A | | | | | 0.28 | 0.34 |
| Kit Cayman no R/A | | | | | | 0.36* |

When the R/A procedure was not carried out on the samples, the AlphaLISA® assay with the monoclonal antibody showed a significant moderate correlation with both the AlphaLISA® assay with the polyclonal antibody (P<0.001; r=0.63) and the Cayman Chemical ELISA kit assay (P<0.001; r=0.51). No significant correlation was found between the AlphaLISA® assay with the polyclonal antibody and the Cayman Chemical ELISA kit assay. When the R/A procedure was carried out, the AlphaLISA® assay with the monoclonal antibody showed a significant moderate correlation with both the AlphaLISA® assay with the polyclonal antibody (P<0.001; r=0.58) and the Cayman Chemical ELISA kit assay (P<0.001; r=0.53). No significant correlation was found between the AlphaLISA® assay with the polyclonal antibody and the Cayman Chemical ELISA kit assay.

REFERENCES

Brandtzaeg et al. (2016). Proteomics tools reveal startlingly high amounts of oxytocin in plasma and serum. Sci Rep, 6, 31693.

López-Arjona et al. (2020). Oxytocin in saliva of pigs: an assay for its measurement and changes after farrowing. Domest Anim Endocrinol, 70, 106384.

MacLean et al. (2018). Validation of salivary oxytocin and vasopressin as biomarkers in domestic dogs. J Neurosci Methods, 293, 67-76.

The invention claimed is:

1. An in vitro method for the detection and quantification of free oxytocin and protein-bound oxytocin able to be released in a reduction/alkylation treatment, in a sample, said method comprising carrying out an assay comprising:

adding to said sample a monoclonal antibody that specifically binds to free oxytocin and protein-bound oxytocin able to be released in a reduction/alkylation treatment, wherein said monoclonal antibody comprises:

a heavy chain CDR1 region consisting of the sequence SEQ ID NO: 6;

a heavy chain CDR2 region consisting of the sequence SEQ ID NO: 8;

a heavy chain CDR3 region consisting of the sequence SEQ ID NO: 10;

a light chain CDR1 region consisting of the sequence SEQ ID NO: 16;

a light chain CDR2 region consisting of the sequence SEQ ID NO: 18; and a light chain CDR3 region consisting of the sequence SEQ ID NO: 20;

determining the amount or concentration of monoclonal antibody bound to free oxytocin and protein-bound oxytocin able to be released in a reduction/alkylation treatment; and determining the amount or concentration of free oxytocin and protein-bound oxytocin able to be released in a reduction/alkylation treatment from the amount or concentration of monoclonal antibody bound to said free oxytocin and to protein-bound oxytocin able to be released in a reduction/alkylation treatment.

2. The method according to claim 1, wherein the variable domain of the heavy chain VH has at least 95% identity to the sequence SEQ ID NO: 3 and the variable domain of the light chain VL has at least 95% identity to the sequence SEQ ID NO: 13.

3. The method according to claim 1, wherein the variable domain of the heavy chain VH consists of the sequence SEQ ID NO: 3 and the variable domain of the light chain VL consists of the sequence SEQ ID NO: 13.

4. The method according to claim 1, wherein the assay is selected from the group consisting of immunofluorescence, immunohistochemistry, immunochromatography, luminescence, homogeneous amplified luminescent proximity assay, immunoelectrotransfer, ELISA, western blot, nephelometry, immunoturbidimetry, lateral chromatography, and microarrays.

5. The method according to claim 1, wherein said monoclonal antibody is attached to a labelling probe or to a sphere attached to a labelling probe.

6. The method according to claim 1, wherein said labelling probe is selected from the group consisting of a fluorophore, a chromophore, a bioluminescent probe, a radioactive probe, an enzyme, and colloidal gold.

7. The method according to claim 1, wherein said sample is selected from the group consisting of serum, plasma, saliva, urine, and cerebrospinal fluid.

8. A monoclonal antibody that specifically binds to free oxytocin and protein-bound oxytocin able to be released in a reduction/alkylation treatment, wherein said monoclonal antibody comprises:

a heavy chain CDR1 region consisting of the sequence SEQ ID NO: 6;

a heavy chain CDR2 region consisting of the sequence SEQ ID NO: 8;

a heavy chain CDR3 region consisting of the sequence SEQ ID NO: 10;

a light chain CDR1 region consisting of the sequence SEQ ID NO: 16;

a light chain CDR2 region consisting of the sequence SEQ ID NO: 18; and a light chain CDR3 region consisting of the sequence SEQ ID NO: 20.

9. The monoclonal antibody according to claim 8, wherein the variable domain of the heavy chain VH has at least 95% identity to the sequence SEQ ID NO: 3 and the variable domain of the light chain VL has at least 95% identity to the sequence SEQ ID NO: 13.

10. The monoclonal antibody according to claim 8, wherein the variable domain of the heavy chain VH consists of the sequence SEQ ID NO: 3 and the variable domain of the light chain VL consists of the sequence SEQ ID NO: 13.

11. A polynucleotide encoding the monoclonal antibody according to claim 8, wherein said polynucleotide comprises the sequence SEQ ID NO: 22, which encodes the variable domain of the heavy chain, and sequence SEQ ID NO: 23, which encodes the variable domain of the light chain.

12. A method of producing the monoclonal antibody of claim 8, said method comprising:

(a) culturing an hydridoma expressing the monoclonal antibody in a culture medium; and (b) purifying the monoclonal antibody from the culture medium.

13. A composition comprising the monoclonal antibody according to claim 8.

14. A kit for detecting free oxytocin and protein-bound oxytocin able to be released in a reduction/alkylation treatment, in a sample, wherein said kit comprises:

(i) the monoclonal antibody according to claim 8; and (ii) buffer solutions to carry out the reactions to form a complex between the monoclonal antibody and the free oxytocin and the protein-bound oxytocin able to be released in a reduction/alkylation treatment.

15. The kit according to claim 14, further comprising reagents for carrying out the reaction to form said complexes between the monoclonal antibody and the free oxytocin and protein-bound oxytocin able to be released in a reduction/alkylation treatment.

16. The monoclonal antibody according to claim 8, wherein said monoclonal antibody is attached to a labelling probe or to a sphere attached to a labelling probe.

17. The monoclonal antibody according to claim 16, wherein said labelling probe is selected from the group consisting of a fluorophore, a chromophore, a bioluminescent probe, a radioactive probe, an enzyme, and colloidal gold.

* * * * *